United States Patent [19]

Uraneck et al.

[11] 3,993,854
[45] Nov. 23, 1976

[54] ORGANOLITHIUM/ALKADIENOL ADDUCTS AS POLYMERIZATION INITIATORS

[75] Inventors: Carl A. Uraneck; Richard L. Smith, both of Bartlesville, Okla.

[73] Assignee: Phillips Petroleum Company, Bartlesville, Okla.

[22] Filed: Oct. 24, 1975

[21] Appl. No.: 625,745

[52] U.S. Cl. .............................. 526/021; 526/173; 526/175; 526/240; 260/77.5 CR; 526/42; 526/54; 526/335

[51] Int. Cl.$^2$ ...................... C08F 8/42; C08F 8/08; C08F 36/14

[58] Field of Search ................ 260/94.2 T, 94.2 M, 260/94.7 A, 83.7, 85.11; 526/20, 21, 173, 175, 240

[56] References Cited
UNITED STATES PATENTS

| | | | |
|---|---|---|---|
| 2,856,391 | 10/1958 | Diem | 260/94.2 |
| 2,951,831 | 9/1960 | Reinhard | 260/80.7 |
| 3,041,320 | 1/1962 | Chapin et al. | 260/82.1 |
| 3,287,333 | 11/1966 | Zelinski | 260/83.7 |
| 3,294,768 | 12/1966 | Wofford | 260/83.7 |
| 3,317,918 | 5/1967 | Foster | 260/83.7 |

FOREIGN PATENTS OR APPLICATIONS 850,894  10/1960  United Kingdom ................ 260/94.2

OTHER PUBLICATIONS

Tetrahedron Letters No. 5, pp. 325–328 (G. Britain), "Organolithium Additions to Allylic Alcohols," by Crandall, et al., (1969).

J. Pol. Science Part A–1; vol. 8, pp. 533–543 (1970), "Effect of Lithium Alkoxide on Polymerization," by Hsieh.

Primary Examiner—William F. Hamrock

[57] ABSTRACT

Adducts of hydrocarbon lithium compounds and alkadienols such as 2,4-pentadien-1-ol are employed in the anionic solution polymerization of polymerizable monomers to produce polymers containing terminal hydroxyl groups.

25 Claims, No Drawings

ORGANOLITHIUM/ALKADIENOL ADDUCTS AS POLYMERIZATION INITIATORS

FIELD OF THE INVENTION

The invention relates to methods to produce polymers containing hydroxyl functional groups. In another aspect the invention relates to polymers containing hydroxy functional groups. In a further aspect, the invention relates to novel lithium-based polymerization initiators. In a still further aspect, the invention relates to methods to prepare novel lithium-based polymerization initiators. In an additional aspect, the invention relates to cured polymers.

BACKGROUND OF THE INVENTION

Polymers with functional groups, such as hydroxyl functional groups, are very useful since such polymers can be cured with a variety of polyfunctional compounds. Liquid, or semisolid polymers, for instance, can be conveniently converted into solid products. Polymers with hydroxyl groups are particularly useful since they can be cured with a system such as a diisocyanate-polyol system to form polyurethane-type rubbers, or can be cured with conventional vulcanization.

New and novel methods of producing polymers with hydroxy functional groups are desired.

BRIEF SUMMARY OF THE INVENTION

We have discovered novel adducts of hydrocarbon lithium compounds and alkadienols. We further have discovered methods of preparing the adducts. We also have discovered that the adducts are effective in the anionic solution polymerization of polymerizable monomers, such as conjugated dienes, to produce novel polymers containing hydroxyl groups. The novel polymers can be cured to produce novel cured stocks.

DETAILED DESCRIPTION OF THE INVENTION

Hydrocarbon lithium compounds are reacted with alkadienols, hydroxyalkyl-substituted conjugated dienes, to produce an adduct. The ratio of the hydrocarbon lithium compound to the hydroxyalkyl-substituted conjugated diene should be the ratio sufficient and effective to form the aforesaid adduct. A slight excess of either reactant is not objectionable.

HYDROXYALKYL-SUBSTITUTED ALKADIENES

The alkadienols, the hydroxyalkyl-substituted conjugated alkadienes, containing one hydroxy group per molecule, can be represented by the following formula:

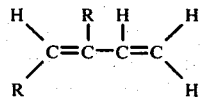

wherein each R represents hydrogen or a hydroxyalkyl group of up to 6 carbon atoms per group, such that said hydroxyalkyl-substituted conjugated alkadiene as per formula (I) contains one hydroxyalkyl group per molecule. The preferred compounds contain a hydroxyalkyl group which is a linear alkylene group wherein the hydroxyl function is connected to a primary carbon atom in the alkylene group. For convenience and reactivity, the alkadienol compounds contain 5 to 10 carbon atoms per molecule, with 5 or 6 carbon atoms per molecule being preferred because of availability and reactivity.

Examples of alkadienols useful in accordance with our invention include: 2,4-pentadien-1-ol, 3,5-hexadien-1-ol, 7,9-decadien-1-ol, 3,5-hexadien-2-ol, 4,6-heptadien-2-ol, 2-methyl-4,6-heptadien-2-ol, 3-methyl-5,7-octadien-2-ol, 2,2-dimethyl-5,7-octadien-1-ol, 2-n-propyl-4,6-heptadien-1-ol, 2-methylene-3-buten-1-ol, 3-methylene-4-penten-1-ol, 7-methylene-8-nonen-1-ol, 3-methylene-1-hexen-4-ol, 4-methylene-5-hexen-2-ol, 2-methyl-4-methylene-5-hexen-2-ol, 3-methyl-5-methylene-6-hepten-2-ol, 2,2-dimethyl-5-methylene-6-hepten-1-ol, 4-methylene-2-n-propyl-5-hexen-1-ol, and the like and mixtures thereof. 2,4-Pentadien-1-ol is the presently preferred compound of Formula I due to availability.

HYDROCARBON LITHIUM COMPOUNDS

Hydrocarbon lithium compounds, which can be employed in the reaction with the alkadienols, include any of the hydrocarbon lithium compounds including the saturated aliphatic, saturated cycloaliphatic, or aromatic hydrocarbon lithium compounds.

For convenience, such hydrocarbon compounds also can be described by a formula $R(Li)_x$ wherein R represents the hydrocarbon radical, which can be saturated aliphatic, saturated cycloaliphatic, or aromatic. The R group has a valence equal to $x$, and $x$ is an integer of 1 to 4. While the R radical size is not limited in size as far as operability is concerned, presently for convenience it will range from 1 to 20 carbon atoms, and most preferred are the saturated aliphatic type containing 1 to 6 carbon atoms, from 1 to 2 lithium atoms, and preferably wherein $x$ is 1 because of availability and reactivity.

These hydrocarbon lithium compounds typically include such as methyllithium, isopropyllithium, sec-butyllithium, tert-butyllithium, n-decyllithium, phenyllithium, naphthyllithium, 4-butylphenyllithium, p-tolyllithium, 4-phenylbutyllithium, cyclohexyllithium, 1,4-dilithiobutane, 1,20-dilithioeicosane, 1,4-dilithiocyclohexane, 1,5-dilithionaphthalene, 1,3,5-trilithiopentane, 1,2,4,6-tetralithiocyclohexane, and the like. Secondary and tertiary alkyllithiums, such as sec-butyllithium and tert-butyllithium presently are preferred because of reactivity and availability.

DILUENT

The diluent employed for the contacting and reacting of the hydrocarbon lithium compound or compounds with the alkadienol or alkadienols can be any of the available saturated aliphatic hydrocarbons (alkanes), saturated cycloaliphatic hydrocarbons or aromatic hydrocarbons, preferably of 5 to 8 carbon atoms per molecule for convenience and availability, typically such as pentane, hexane, cyclohexane, benzene, toluene, xylene, and the like, alone or admixture. For convenience, the diluent can be employed in amounts ranging from such as 10 to 500 parts by weight per part of hydrocarbon lithium, about 20 to 150 parts by weight presently being preferred because of convenience and consistency of subsequent reaction mixture. Cyclohexane presently is a preferred diluent because of ready availability, ease of subsequent removal, cost, and evironmental consideration.

The adduct initiators are prepared by contacting the hydrocarbon lithium compound with the alkadienol in any convenient manner, preferably in the aforesaid diluent, under suitable reaction conditions of temperature and pressure as desired, with a temperature control means where necessary to avoid excessive reactions, temperatures, or pressures, and conveniently in any suitable stirred reactor capable of maintaining substantially anhydrous conditions, and preferably under an inert atmosphere such as nitrogen, since traces of moisture, oxygen, and the like, are known to be deleterious to lithium initiators in general.

As exemplary, a ratio of hydrocarbon lithium compound:alkadienol in the range of about 1.5:1 to 3.5:1, equivalents of lithium per mole of alkadienol are suitable. Presently preferred is a ratio of about 1.5:1 to 2.5:1, since large excesses of either reactant are not necessary. Most preferred for highest efficiency is a ratio of about 2:1 lithium equivalents per mole of alkadienol.

The reaction is quite exothermic, and controlled temperature may be desirable. Contacting can be at any suitable temperature, such as by contacting the reactants in the temperature range of about $-30°$ C to $70°$ C, presently preferred about $-10°$ C to $+30°$ C in order to maintain reasonable reaction rates and yet minimize the heating or cooling capacity required for temperature control. It is convenient to permit contacting of the reactants at a temperature, such as room temperature or up to about $30°$ C, and allow the contacting reaction to occur adiabatically, such that the temperature may reach a maximum of about $50°$ to $70°$ C or upwards, depending on the reactants and heat transfer properties of the system. Any convenient pressures can be employed sufficient to maintain substantially liquid phase conditions.

Time employed for the preparation of the adducts can vary widely, depending on temperatures and reactivity of the particular reactants chosen. Anywhere from a few seconds to upwards of 24 hours or more may be required. We have found generally sufficient reaction times of about 2 minutes to 2 hours for most purposes.

POLYMERIZATION

Our novel adduct initiators prepared in accordance with the method of our invention can be employed without further treatment, thus without prior isolation or purification, or separation from the diluent. The adducts can be prepared, for example, in the polymerization reactor means prior to introduction of polymerizable monomers; or the adducts can be separately prepared and transferred to the polymerization system as a slurry. Alternatively, however, the adducts, which are normally insoluble in hydrocarbon diluents, can be isolated, if desired, and purified by any conventional means such as filtration and washing with hydrocarbon solvent, though precautions are necessary to protect the material from moisture and air.

POLYMERIZABLE MONOMERS

Polymerizable monomers employed in the polymerization aspect of our invention are those vinylidine group containing monomers polymerizable with lithium-based initiators in anionic solution polymerization systems. These include conjugated dienes, monovinyl-substituted aromatic compounds, and a variety of polar monomers.

The conjugated dienes are the hydrocarbon conjugated dienes, preferably containing 4 to 12 carbon atoms per molecule, more preferably for availability 4 to 8 carbon atoms per molecule, and presently preferred for commercial use are 1,3-butadiene and isoprene. Other examples of typical conjugated dienes in the group are piperylene, 2,3-dimethyl-1,3-butadiene, 3-butyl-1,3-octadiene, 2-phenyl-1,3-butadiene, and the like, alone or in admixture. The conjugated dienes can be polymerized into homopolymers, or copolymers, or can be copolymerized with other vinylidene-group containing monomers.

Among the other polymerizable monomers are the monovinyl-substituted aromatic compounds, preferably of the hydrocarbon type, of 8 to 12 carbon atoms per molecule because of availability and reactivity. These include the presently preferred commercially available styrene, as well as 1-vinylnaphthalene, 2-vinylnaphthalene, 3-methylstyrene, 4-dodecylstyrene, 4-cyclohexylstyrene, 2-ethyl-4-benzylstyrene, 4-p-tolylstyrene, and the like, alone or in admixture. Those monovinyl-substituted aromatic hydrocarbons can be homopolymerized, copolymerized, or copolymerized with other polymerizable monomers.

Among the polar monomers which can be polymerized to form homopolymers or copolymers with each other or copolymerized with the above-described conjugated dienes and/or monovinyl-substituted aromatic hydrocarbon compounds, are the vinyl pyridines, vinylquinolines, vinyl isoquinolines, alkyl esters of methacrylic acid, alkyl esters or ethacrylic acid, nitriles, and the like.

Examples include the pyridine, quinoline, and isoquinoline derivatives corresponding to the above-described monovinyl-substituted aromatic hydrocarbons, including such as 2-vinylpyridine, 4-vinylpyridine, 3-vinylisoquinoline, and the like.

Other polar monomers include methyl acrylate, ethyl acrylate, methyl methacrylate, butyl methacrylate, acrylonitrile, methacrylonitrile, N,N-dimethylacrylamide, and similar acrylic and alkacrylic acid ester, nitriles, and N,N-di-substituted amides, and also such as vinylfuran, and n-vinylcarbazole.

POLYMERIZATION PROCESS

Contacting of one or more of the monomers described with the adduct can be conducted under conditions generally practiced in the anionic solution polymerization arts. Contacting of the monomers with the adducts can be conducted preferably in the presence of a hydrocarbon diluent, such as any of those described for the preparation of the adduct itself.

The amount of initiator employed can vary over a wide range, dependent in general on the desired molecular weight of the polymer, as well as on monomer reactivity, and the like, as is known relative to the monomers above-described. The amount of initiator to be employed as an exemplary range would be from about 0.5 to 75 milliequivalents of lithium per 100 per parts by weight of monomer, presently preferred about 25 to 65 in order to obtain polymers from the preferred monomers with generally useful properties.

The monomers can be contacted with the adduct in the hydrocarbon diluent under suitable reaction conditions, such as a contacting temperature of about $40°$ to $100°$ C, preferably about $50°-75°$ C in order to provide a reasonable reaction rate at temperatures readily attainable and controllable in available reactors, at any convenient pressure sufficient to maintain a substantially liquid phase, for a wide range of time such as several minutes to several hours.

The resulting polymer are characterized as containing carbon-lithium moieties on one end of the polymer molecule, with carbon-oxygen-lithium moieties on the other end of the polymer molecule. Polymerization can be terminated at this stage, if desired, so as to convert the carbon-lithium polymer ends to functional groups such as hydroxyl, carboxyl, and the like, employing agents known to be useful in this respect, such as epoxides, imines, orthoformates, carbon dioxide, and the like. Epoxides produce hydroxyl groups; imines produce amine groups; carbon dioxide carboxyl groups; and so on as is known in the art.

If desired, at the completion of the polymerization interval, the so-called living polymers, polymers containing carbon-lithium moieties and thus capable of propagating further polymerization, can be coupled using a variety of coupling agents as known in the art, such as any of the polyfunctional agents such as silicon polyhalides, the polyepoxides, the tin polyhalides, polyisocyanates, polyesters, polyimines and polyaldehydes. The polyfunctional treating agent can be employed in the range of about 0.05 to 2 and preferably 0.5 to 1.5 equivalents per gram atom of initiating lithium groups. Depending on the extent of functionality in the coupling agent, the result is a higher molecular weight linear, branched, or radial polymer. The carbon-lithium moieties of the aforesaid living polymers tend to react preferentially with such coupling agents before the carbon-oxygen-lithium moieties react. If it is desired to protect the oxygen-lithium bonds from reaction during the coupling step, stoichiometric amounts of coupling agents added with suitable and efficient mixing are to be preferred.

At the completion of the entire polymerization reaction, and coupling step if employed, the total reaction mixture then is treated to inactivate initiator and lithium moieties, so as to provide the desired terminal hydroxyl group functions in the polymer. Any suitable treating method can be so employed, such as adding water, or a lower alcohol such as isopropyl alcohol, and the like, for inactivation of remaining available lithium. Such additives also tend to coagulate the polymer when employed in sufficient amount. The polymers can be recovered by any suitable means such as coagulation with the aforesaid alcohol, by steam stripping of solvent, and the like, followed by filtration, drying, as may be necessary or commercially suitable.

Polymers prepared in accordance with this invention can be obtained as liquids, semisolids, or solid rubbery materials containing a hydroxyl group on at least one end of the polymer molecule, and, if desired, a different functional group also on the other end.

Where desired, polymers can be further cured using diisocyanatepolyalcohol systems known to the art to form polyurethane-like compositions. Conventional vulcanization systems can be employed to cure polymers prepared to this invention. Vulcanization accelerators, reinforcing agents, fillers, extenders, can be added to the polymer as is known in the art.

Polyurethane-like compositions can be prepared from the polymers obtained using the initiating adduct species of this invention by treating the polymers with a polyisocyanate, preferably a diisocyanate so as to convert the polymer hydroxyl groups into urethane-type linkages. An excess of polyisocyanate normally is employed, and a chain extender, such as a polyol, preferably is added to convert the excess isocyanate groups into urethane-type linkages. Molding the resulting incompletely cured polymer under heat and pressure completes the conversion of the polymers into firm gumstocks.

Many known polyisocyanates of general formula $R(NCO)_x$ wherein R is a hydrocarbyl radical of valence x having up to about 20 carbon atoms, and wherein x is an integer having the value of from 2 to 4 are useful in the curing of the hydroxyl-containing polymers. Examples of commercially available diisocyanates are 2,4-tolylene diisocyanate (TDI), diphenylmethane diisocyanate (MDI), hexamethylene diisocyanate and the like. Aryl diisocyanates such as TDI and MDI presently are preferred.

Many chain extenders are known in the art and are useful in the curing of the polymers prepared in accordance with this invention. Examples of commercially available chain extenders include 1,4-butanediol, 2-ethyl-1,3-hexanediol, trimethylolpropane, triisopropanolamine, N,N-bis(2-hydroxypropyl)-aniline, 3,3'-dichlorobenzidine and the like. Especially preferred are the diols, such as N,N-bis(2-hydroxypropyl)aniline.

It is sometimes desirable to include accelerators in the curing system which are well known in the art to accelerate the reaction of isocyanates with hydroxyl groups. Such accelerators include dibutyltin dilaurate, stannous octoate, triethylene diamine, and the like.

The chain extenders, preferably diols, normally are used in amounts ranging from about 0 to 5, preferably about 1 to 3, equivalents of extender hydroxy per equivalent of polymer hydroxy groups. The polyisocyanates, preferably diisocyanates, normally are employed in amounts ranging from about 1 to 1.15, preferably about 1 to 1.05, equivalents of isocyanate per equivalent of total hydroxy (polymer hydroxy plus extender hydroxy). Accelerators normally are used in amounts ranging from 0 to about 0.5, preferably about 0.15 to 0.25, parts by weight per one hundred parts by weight polymer.

Subsequent curing of the resultant polymer-polyisocyanate-chain extender reaction product can be carried out at any temperature and pressure for any time which results in the desired product. It currently is useful to cure the reaction product at about 95° to 125° C and at about 15,000 to 20,000 psig for about 1 to 2 hours.

EXAMPLES

Examples following are intended to assist in an understanding of our invention, and are to be considered as a part of our specification and disclosure. Exemplary species, amounts, relationships, are to be considered exemplary, and not limitative.

EXAMPLE I

The following run illustrates the preparation and analysis of the reaction products from 2,4-pentadien-1-ol and sec-butyllithium.

In a reactor under a nitrogen atmosphere were mixed 2.45 mmoles 2,4-pentadien-1-ol and 6.61 mmoles sec-butyllithium in sufficient cyclohexane to give 28 ml of solution. A white precipitate formed immediately after which the slurry turned a light orange color. The system was maintained at 27° C for 30 minutes.

Hydrolysis of a portion of the above slurry with acetic acid and subsequent analysis of the hydrolyzate by gas-liquid chromatography (glc) showed the presence of a C- alcohol and some heavier alcohols. The presence of a C alcohol indicated the formation of a 2/1 sec-butyllithium/2,4-pentadienol adduct such as according to the following possible reaction scheme:

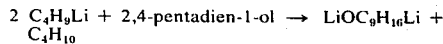

Glc analysis of the original slurry showed the presence of butane which was increased by 20 percent by subsequent hydrolysis of the slurry with water. These data indicated that 13 percent of the original sec-butyllithium was unreacted.

Analysis of the original slurry for carbon-lithium bonds showed 2.32 mmoles of carbon-lithium bonds. Consideration of this and of the above data indicate that the slurry contained 1.46 mmoles of species, other than sec-butyllithium, containing carbon-lithium bonds.

EXAMPLE II

The following run illustrates the use of the reaction products as described in Example I to initiate polymerization of 1,3-butadiene and subsequent characterization of the resultant polymer.

The reaction product of sec-butyllithium (32 mmoles) and 2,4-pentadien-1-ol (12 mmoles) in 71 ml of cyclohexane solution was prepared as described in Example I. The resultant slurry was transferred to a reactor containing 325 ml cyclohexane and 40 gm 1,3-butadiene under a nitrogen atmosphere. The reactor was maintained at 70° C for 30 minutes with continuous agitation. The resultant polymer solution was acidified with hydrochloric acid, then washed with aqueous isopropyl alcohol (50 weight percent water) until neutral. Solvent was removed under vacuum with a nitrogen purge. Polymer was obtained representing 89 percent conversion of monomer to polymer.

The isolated polymer possessed the following properties:

| | |
|---|---|
| Trans Unsaturation, %[a] | 51 |
| Vinyl Unsaturation, %[a] | 9 |
| $M_w$[b] | 54,000 |
| $M_n$[b] | 24,000 |
| Heterogeneity Index[b] | 2.3 |
| Inherent Viscosity[c] | 0.83 |
| Gel, %[c] | 0 |
| Hydroxyl, wt. %[d] | 0.19 |

[a]Unsaturation by infrared analysis.
[b]Determined by gel permeation chromatography.
[c]Determined as described in U.S. Patent 3,278,508, column 20, Note a, using tetrahydrofuran as solvent.
[d]Determined as described in Anal. Chem. 31, 1808 (1959).

The above data illustrate that the above-described reaction product initiated polymerization of 1,3-butadiene to give a polybutadiene containing hydroxyl groups.

The disclosure, including data, illustrate the value and effectiveness of our invention. The examples, the knowledge and background of the field of the invention and general principles of chemistry and other applicable sciences, have formed the bases from which the broad descriptions of the invention including the ranges of conditions and generic groups of operant components have been developed, which have formed the bases for our claims here appended.

We claim:

1. A polymerization process which comprises polymerizing at least one vinylidene group-containing monomer under anionic solution polymerization conditions in a hydrocarbon diluent employing a lithium-based adduct polymerization initiator, effective polymerization conditions of temperature, pressure, and time, and effective ratios of said lithium-based adduct, wherein said lithium-based adduct polymerization initiator is the reaction product of a hydrocarbon lithium compound with a monohydroxyalkyl-substituted conjugated alkadiene, which is represented by the formula:

wherein R is hydrogen or a hydroalkyl group such that (I) contains a single hydroxyalkyl group and wherein said (I) contains 5 to 10 carbon atoms per molecule.

2. The process according to claim 1 wherein said monohydroxyalkyl-substituted conjugated alkadiene is selected from the group consisting of 2,4-pentadien-1-ol, 3,5-hexadien-1ol, 7,9-decadien-1-ol, 3,5hexadien-2ol, 4,6-heptadien-2ol, 2-methyl-4,6-heptadien-2-ol, 3-methyl-5,7-octadien-2ol, 2,2-dimethyl-5,7-octadien-1-ol, 2-n-propyl-4,6-heptadien-1ol, 2-methylene-3-buten-1-ol, 3-methylene-4-penten-1-ol, 7-methylene-8-nonen-1-ol, 3-methylene-1-hexen-4-ol, 4-methylene-5-hexen-2-ol, 2-methyl-4-methylene-5-hexen-2-ol, 3-methyl-5-methylene-6-hepten-2-ol, 2,2-dimethyl-5-methylene-6-hepten-1-ol, or 4-methylene-2-n-propyl-5-hexen-1-ol.

3. The process according to claim 1 wherein said hydrocarbon lithium compound is represented by $RLi_x$ wherein R is a hydrocarbon radical which is a saturated aliphatic, saturated cycloaliphatic, or aromatic radical.

4. The process according to claim 3 wherein said hydrocarbon lithium compound is selected from the group consisting of methyllithium, isopropyllithium, sec-butyllithium, tert-butyllithium, n-decyllithium, phenyllithium, naphthyllithium, 4-butylphenyllithium, p-tolyllithium, 4-phenylbutyllithium, cyclohexyllithium, 1,4-dilithiobutane, 1,20-dilithioeicosane, 1,4-dilithiocyclohexane, 1,5-dilithionaphthalene, 1,3,5-trilithiopentane, or 1,2,4,6-tetralithiocyclohexane.

5. The process according to claim 3 wherein said hydrocarbon lithium compound is a secondary or tertiary alkyllithium.

6. The process according to claim 5 wherein said hydrocarbon lithium compound is sec-butyllithium or tert-butyllithium.

7. The process according to claim 4 employing a ratio of said hydrocarbon lithium compound: said monohydroxyalkyl substituted conjugated alkadiene in the range of about 1.5:1 to 3.5:1.

8. The process according to claim 7 wherein said ratio is in the range of about 1.5:1 to 2.5:1.

9. The process according to claim 8 wherein said ratio is about 2:1.

10. The process according to claim 4 wherein said contacting of said hydrocarbon lithium compound with said alkadienol is conducted in a hydrocarbon diluent, wherein said diluent represents about 10 to 500 parts by weight per part of said hydrocarbon lithium compound.

11. The process according to claim 10 wherein said contacting is conducted at a temperature in the range of about −30° to 70° C, under a pressure sufficient to maintain reactants and diluents substantially in the liquid phase, for a time sufficient for production of said adducts.

12. The process according to claim 1 wherein said vinylidene group-containing monomer is a conjugated dien, monovinyl-substituted aromatic hydrocarbon, or both.

13. The process according to claim 12 wherein said conjugated diene hydrocarbon contains 4 to 12 carbon atoms per molecule; said monovinyl-substituted aromatic compound contains 8 to 12 carbon atoms per molecule.

14. The process according to claim 12 wherein said polymerization process employs said adduct in an amount sufficient to provide about 0.5 to 75 milliequivalents of lithium per 100 parts by weight of monomer.

15. The process according to claim 14 wherein said polymerization is conducted at a temperature in the range of about 40° to 100° C, under a pressure sufficient to maintain reactants and diluents substantially in the liquid phase, and wherein said adduct is employed in an amount sufficient to provide about 25 to 65 milliequivalents of lithium per 100 parts by weight of monomer.

16. The process according to claim 15 wherein said alkadienol is 2,4-pentadien-1-ol and said hydrocarbon lithium compound is sec-butyllithium.

17. The process according to claim 16 wherein said vinylidene group-containing monomer is 1,3-butadiene.

18. The process which comprises reacting 2,4-pentadien-1-ol with sec-butyllithium in a mole ratio of about 8:3 sec-butyllithium:2,4-pentadien-1-ol, in a hydrocarbon diluent comprising cyclohexane, and thereafter contacting the resulting reaction product with 1,3-butadiene under polymerization conditions under a nitrogen atmosphere employing a hydrocarbon diluent comprising cyclohexane for a time sufficient to substantially polymerize said 1,3-butadiene, and treating the resulting butadiene polymer solution with hydrochloric acid, followed by aqueous isopropanol, and recovering the resulting polymer as a hydroxy-containing polymer product.

19. The polymerization process which comprises polymerizing at least one polymerizable monomer which is a conjugated diene, monovinyl-substituted aromatic hydrocarbon, or both, under anionic solution polymerization conditions of temperature, pressure, and time, in a hydrocarbon diluent, and employing an effective amount of a lithium-based adduct initiator,
wherein said lithium-based adduct initiator is the reaction product of a hydrocarbon lithium compound with a monohydroxyalkyl-substituted conjugated alkadiene which is represented by the formula

wherein R is hydrogen or a hydroalkyl group such that (I) contains a single hydroxyalkyl group and wherein said (I) contains 5 to 10 carbon atoms per molecule.

20. The polymerization process according to claim 19 wherein said polymerization monomer is a said conjugated diene, and said conjugated diene is a hydrocarbon containing 4 to 12 carbon atoms per molecule.

21. The polymerization process according to claim 20 wherein said hydrocarbon lithium compound contains up to 20 carbon atoms per molecule.

22. The process according to claim 21 wherein said conjugated diene is butadiene, said hydrocarbon lithium compound is sec-butyllithium or tert-butyllithium, said monohydroxyalkly-substituted conjugated alkadiene is 2,4-pentadien-1-ol.

23. Polymers prepared by the process of claim 1.

24. The polymers according to claim 23 wherein said vinylidene group-containing monomer is a hydrocarbon conjugated diene or monovinyl-substituted aromatic hydrocarbons.

25. The polymers according to claim 24 wherein said vinylidene group-containing monomer is a conjugated diene, monovinyl-substituted aromatic hydrocarbon, or both; and wherein said conjugated diene hydrocarbon contains 4 to 12 carbon atoms per molecule, and said monovinyl-substituted aromatic compound contains 8 to 12 carbon atoms per molecule.

* * * * *